(12) United States Patent
Abovitz et al.

(10) Patent No.: US 7,139,418 B2
(45) Date of Patent: Nov. 21, 2006

(54) FLUOROSCOPIC REGISTRATION ARTIFACT WITH OPTICAL AND/OR MAGNETIC MARKERS

(75) Inventors: Rony A. Abovitz, Hollywood, FL (US); Brandon D. Larocque, Sunrise, FL (US); Julio J. Santos-Munne, Glenview, IL (US)

(73) Assignees: Z-Kat, Inc., Ft. Lauderdale, FL (US); Biomet Manufacturing Corp., Warsaw, IN (US)

( * ) Notice: Subject to any disclaimer, the term of this patent is extended or adjusted under 35 U.S.C. 154(b) by 527 days.

(21) Appl. No.: 09/963,873

(22) Filed: Sep. 25, 2001

(65) Prior Publication Data

US 2003/0059097 A1    Mar. 27, 2003

(51) Int. Cl.
*G06K 9/00* (2006.01)
(52) U.S. Cl. .................. 382/132; 382/294; 600/414; 600/426
(58) Field of Classification Search ................ 600/414, 600/426; 382/128, 132, 294
See application file for complete search history.

(56) References Cited

U.S. PATENT DOCUMENTS

| | | | |
|---|---|---|---|
| 5,389,101 A | | 2/1995 | Heilbrun et al. |
| 5,394,457 A | * | 2/1995 | Leibinger et al. ........... 378/162 |
| 5,397,329 A | * | 3/1995 | Allen ........................... 606/73 |
| 5,729,129 A | * | 3/1998 | Acker .................... 324/207.12 |
| 5,799,055 A | | 8/1998 | Peshkin et al. |
| 5,951,475 A | | 9/1999 | Gueziec et al. |
| 6,165,181 A | * | 12/2000 | Heilbrun et al. ............ 606/130 |
| 6,405,072 B1 | * | 6/2002 | Cosman ..................... 600/426 |

FOREIGN PATENT DOCUMENTS

| | | |
|---|---|---|
| WO | WO 97/40766 | 11/1997 |
| WO | WO 98/35720 | 8/1998 |

* cited by examiner

*Primary Examiner*—Bhavesh M. Mehta
*Assistant Examiner*—Craig W. Kronenthal

(57) ABSTRACT

A registration artifact (10) for use in registering two or more fluoroscopic images includes a plurality of radio opaque spheres (12, 14, 16) and a plurality of trackable markers, such as optical reflectors (20, 22, 24 and 26), mounted to a radio transparent body (11). A tracking system locates the position of registrable artifact using the trackable markers for registering the fluoroscopic images with respect to a known frame of reference.

12 Claims, 3 Drawing Sheets

FLUOROSCOPIC REGISTRATION ARTIFACT WITH OPTICAL AND/OR MAGNETIC MARKERS

TECHNICAL FIELD OF THE INVENTION

The invention relates to image guided surgical and interventional systems.

BACKGROUND OF THE INVENTION

Conventional fluoroscopic registration artifacts have X-ray transparent bodies holding radio-opaque fiducials in predetermined and fixed positions on the registration artifact. The fiducials show up as distinct dots on an X-ray and used to coordinate and register to a common coordinate system multiple X-ray images of a patient taken from different perspectives. The registration artifact remains fixed in position from one image to the next in order to register the images, as an assumption is made that the fiducials in the respective images are in the same positions.

In certain situations, it is advantageous or necessary to relocate the registration artifact. For example, in some instances it is difficult to fit the registration artifact and the relevant anatomy within the fluoroscopic field in the fluoroscopic images due to the particular anatomy or physical configuration of the patient. An obese patient may present such challenges, for example.

One solution has been to track the position of fluoroscope in an operating room rather than use a registration artifact. However, tracking the fluoroscope requires expensive modifications to the fluoroscope.

SUMMARY OF THE INVENTION

According to the invention, fluoroscopic images are registered using a registration artifact that may be relocated. The registration artifact, in which a plurality of radio-opaque fiducials are mounted in a known geometric relationship, includes a plurality of markers having a known relationship to the artifact. The positions of the markers, and thus the position of the registration artifact, are tracked by a tracking system. Examples of such tracking systems include passive and active optical, magnetic and acoustic systems. The position of the registration artifact with respect to a known coordinate frame is determined by the tracking system. Therefore, the registration artifact need not be kept in a fixed location in order to register the images. Rather, the registration artifact may be moved as necessary to fit the registration artifact into an image, and no modification of the fluoroscope is necessary.

BRIEF DESCRIPTION OF THE DRAWINGS

For a more complete understanding of the present invention, the objects and advantages thereof, reference is now made to the following descriptions taken in connection with the accompanying drawings in which.

DETAILED DESCRIPTION OF THE DRAWINGS

The preferred embodiment of the present invention and its advantages are best understood by referring to FIGS. 1 through 5 of the drawings, like numerals being used for like and corresponding parts of the various drawings in a known geometric relationship.

Figure 1:
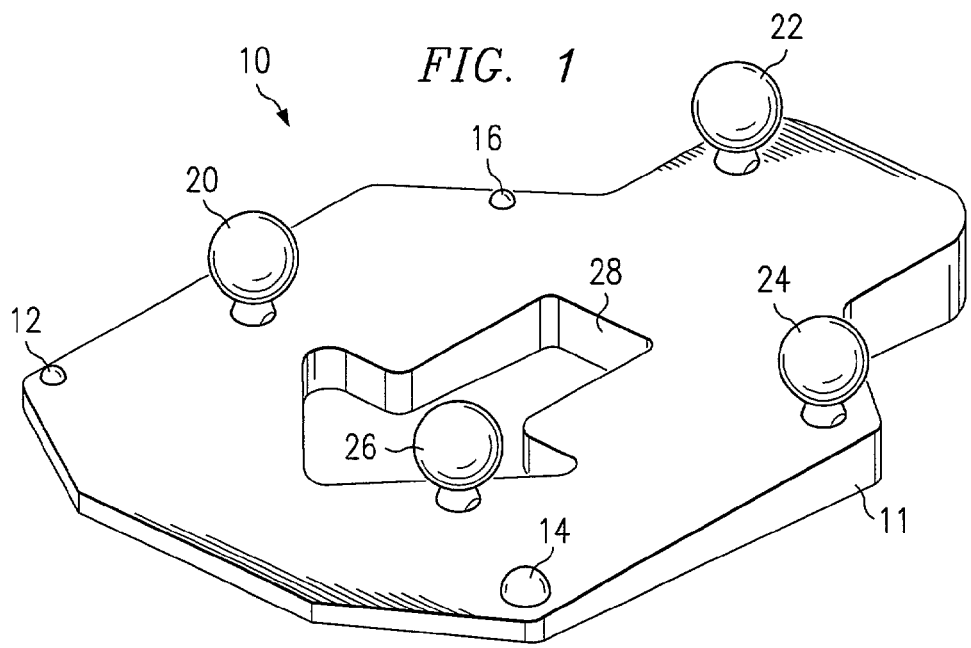
FIG. 1 is a perspective view of an embodiment of a registration artifact.

Referring to FIG. 1, registration artifact 10 includes a radio-transparent body 11 upon which radio-opaque fiducials 12–16 are mounted. Also mounted to the registration artifact 10 are a plurality of markers 20–26 that may be located and tracked using a tracking system. For example, trackable markers 20–26 may be active infrared emitting diodes (IREDs), reflective spheres, magnetically trackable objects, or other spacially trackable objects. Registration artifact 10 may also include a direction indicator 28 to aid in the positioning of the artifact for a procedure. In the embodiment shown, direction indicator 28 is an opening in the shape of an arrow formed in the body 11 of registration artifact 10.

Optically trackable markers may be imaged and tracked in the infrared spectrum or visible spectrum by cameras. The location of magnetically trackable markers are detected by measuring the disturbance of the magnetic field. The cameras and detectors have a much wider field of "view" than the typical fluoroscopy images. An advantage of using magnetic markers is that a line-of-sight between the camera/detector and each of the markers is not required. This may provide more flexibility in how the surgical instruments, robotic arms that assist with surgery, the patient, and a surgical team are positioned.

Figure 2:
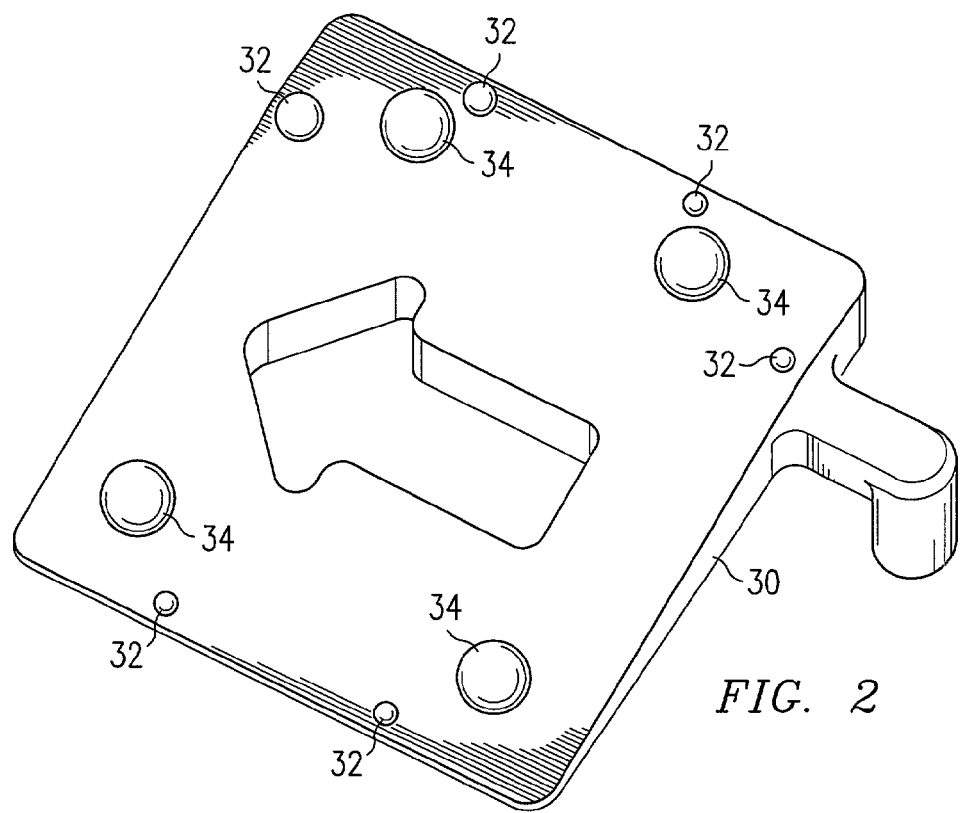
FIG. 2 is a perspective view of a second embodiment of a registration artifact.

Referring to FIG. 2, a second embodiment of a registration artifact 30, like the registration artifact of FIG. 1, includes a plurality of radio-opaque fiducials 32 arranged in a predetermined geometric relationship and a plurality of trackable markers 34 arranged in a known geometric relationship.

Figure 3:
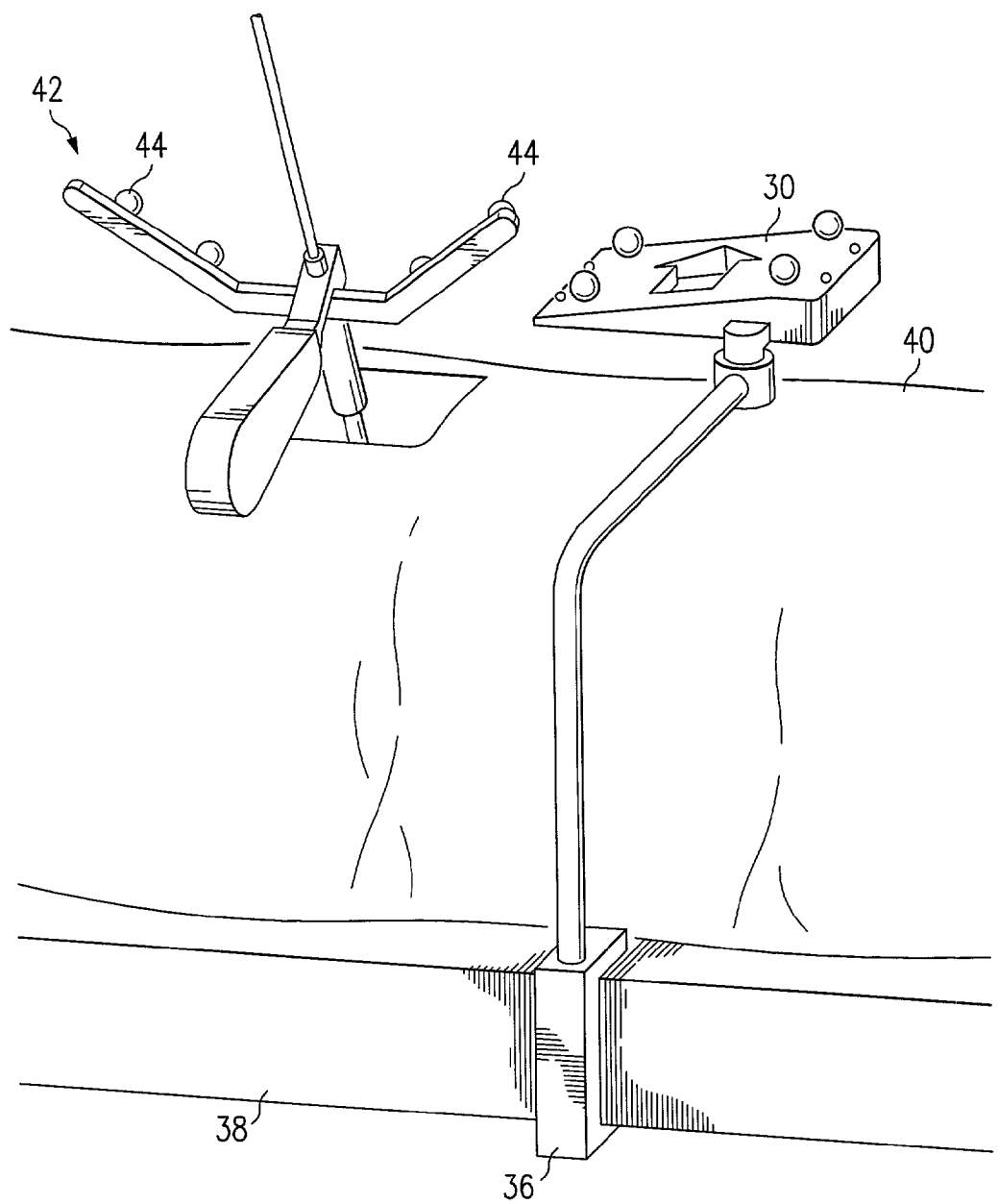
FIG. 3 is a diagram showing the registration artifact being located over a relevant anatomy of a patient with a drill guide according to the teachings of the present invention.
Figure 4:
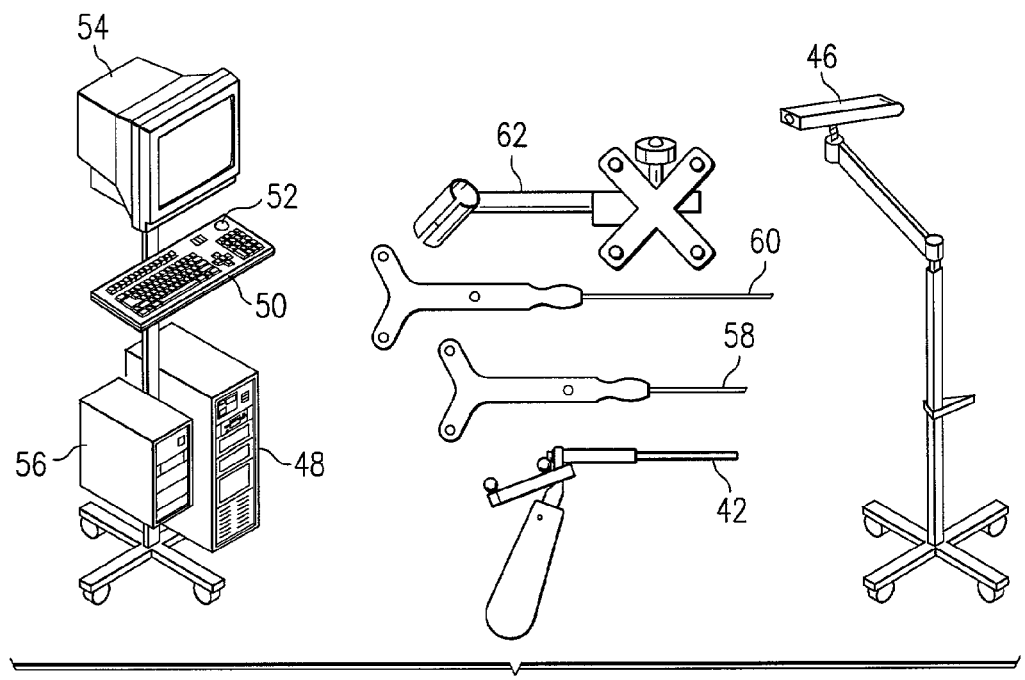
FIG. 4 is a diagram showing some of the tools that may be used in conjunction with the registration artifact according to the teachings of the present invention.
Figure 5:
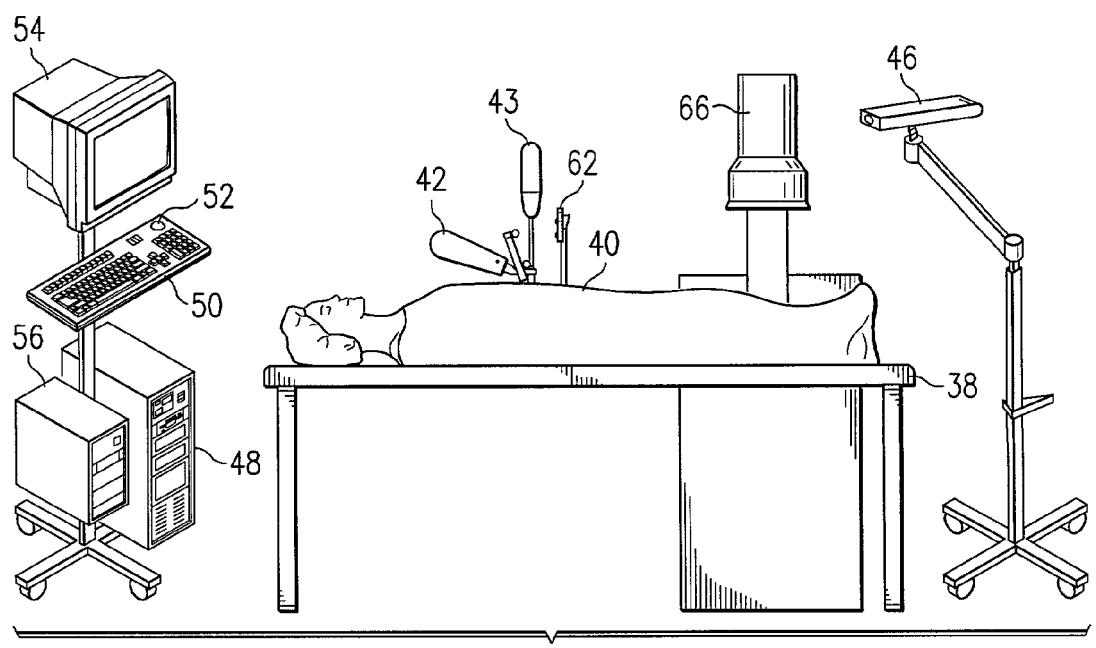
FIG. 5 is a diagram showing an operating room set up according to the teachings of the present invention.

Referring to FIGS. 3–5, registration artifact 30 is mounted on a bracket 36 that clamps to a table 38 on which torso 40 of a patient rests. The bracket allows the artifact to be positioned in the field of view of C-arm fluoroscope 66. The registration artifact may be placed in any other suitable structure. As an example only, drill guide 42 is placed adjacent an entry opening in the patient's torso with a drill 43 being inserted. The drill guide includes a frame on which a plurality of trackable markers, in the form of infrared reflective spheres 44, are attached in a known geometric relationship to the axis and end point of the drill guide. The position of the axis and end point of the drill guide are registered to fluoroscopic images taken with registration artifact 30 in the field of view.

Referring only to FIG. 4, elements of an image guide surgical system include an optical tracking system and related surgical instruments. Optical tracking systems are well known. Other types of tracking systems include magnetic, fiber-optic and acoustic tracking systems. Optical tracking systems typically include a camera system 46 that senses the positions of trackable markers within its field of view that transmit or reflect infrared or other electromagnetic radiation that is not harmful to persons. The signals from optical camera system are processed using a program running on computer 48. The programs locate the positions of trackable markers and determine the position of an object to which the markers are attached with respect to a known coordinate system or reference frame. This position can be used by the computer to generate, for example, a representation of the object that is displayed on a fluoroscopic image of the patient in an accurate spatial relationship with the patient's anatomy for guiding the positioning of the object. The computer includes a keyboard 50 and trackball 52, both of which function as input devices, a monitor 54 for display images and a backup power supply. Surgical instruments include in addition to drill guide 42, probes 58 and 60. These instruments are mounted with trackable markers. Tracker 62 also includes a plurality of trackable markers mounted in a known relationship. It may be clamped to other objects that do not have integrally mounted trackable markers.

Referring back to FIGS. 3–5, fluoroscopic images of the patient's anatomy are captured from at least two different angels using C-arm fluoroscope with a registration artifact in the field of view. As explained in U.S. Pat. No. 5,799,055, entitled *Apparatus and Method for Planning a Stereotactic Surgical Procedure Using Coordinated Fluoroscopy,* issued on Aug. 25, 1998 to Peshkin et al., which is incorporated herein by reference, the fluoroscopic images are registered by locating the positions of the fiducials in the images. However, using this method requires the fiducials to remain in the same position.

When registration artifact 10 is used, the registration artifact no longer needs to remain in a same position in multiple fluoroscopic images. The position of markers on the registration artifact is tracked between images using a tracking system, such as the optical tracking system shown in the figures or other type of tracking system, depending on the type of trackable markers used. This information is used to adjust or compensate for the movement of the registration artifact between the images when registering multiple fluoroscopic images. Therefore, the position of the registration artifact in each image is known. The registration artifact can even be moved to another object, such as a surgical tool on the end of a robotic arm, and its new location tracked and calculated relative to the relevant anatomy of the patient.

While the invention has been particularly shown and described by the foregoing detailed description, it will be understood by those skilled in the art that various changes, alterations, modifications, mutations and derivations in form and detail may be made without departing from the spirit and scope of the invention.

What is claimed is:

1. A method for registering fluoroscopic images comprising:
    positioning a registration artifact in a first location, the registration artifact including a plurality of radio-opaque fiducials arranged in a known geometric relationship and a plurality of trackable markers disposed in a known geometric relationship to the fiducials;
    capturing a first fluoroscopic image of a patient and the radio-opaque fiducials with the registration artifact in the first location:
    determining positions of the trackable markers with respect to a known coordinate frame when the registration artifact is in the first location using a tracking system, the tracking system being separate from the patient and a fluoroscope;
    determining positions of the radio-opaque fiducials in the first fluoroscopic image with respect to the known coordinate frame of the determined positions of the trackable markers;
    relocating the registration artifact to a second location:
    capturing a second fluoroscopic image of the patient and the radio-opaque fiducials with the registration artifact in the second location:
    determining positions of the trackable markers with respect to the known coordinate frame when the registration artifact is in the second location using the tracking system;
    determining positions of the radio-opaque fiducials in the second fluoroscopic image with respect to the known coordinate frame of the determined positions of the trackable markers;
    registering the first and second fluoroscopic images using the positions of the fiducials in each fluoroscopic image and the determined positions, with respect to the known coordinate frame, of the trackable markers.

2. The method of claim 1 wherein the registration artifact for use in registering fluoroscopic images includes:
    a plurality of the radio-opaque fiducials carried by a radio-transparent support structure in a known geometric relationship; and
    a plurality of the trackable markers depending from the support structure in a known geometric relationship to the fiducials.

3. The method of claim 1, wherein at least one of the first and second locations of the registration artifact is independent of the patient.

4. An image guided surgery system comprising:
    a registration artifact, including a plurality of radio-opaque fiducials associated with a radio-transparent body in a known geometric relationship, and a plurality of trackable markers depending from the registration artifact in a known geometric relationship to the fiducials;
    a tracking system for determining positions of the trackable markers within a known reference frame, the tracking system being separate from a patient and a fluoroscope; and
    a computer in communication with the tracking system for receiving information on the positions of the trackable markers, wherein the computer is programmed to:
        register first and second images of the patient and the registration artifact, the registration artifact being disposed in a first location in the first image and a second location in the second image, and
        compensate for changes in position of the registration artifact from the first location to the second location when registering the first and second images.

5. The image guided surgery system of claim 4, wherein the trackable markers include an infrared emitting diode (IRED).

6. The image guided surgery system of claim 4, wherein the trackable markers include a reflective sphere to reflect infrared radiation.

7. The image guided surgery system of claim 4, wherein the trackable markers include optically trackable markers.

8. The image guided surgery system of claim 4, wherein at least one of the first and second locations of the registration artifact is independent of the patient.

9. The image guided surgery system of claim 4, further including:
    a patient table, the registration artifact including a mounting assembly for mounting the artifact to the table at a selectively adjustable location relative to the patient.

10. The image guided surgery system of claim 9, further including:
    a fluoroscope movably mounted relative to the table.

11. The image guided surgery system of claim 9, further including a surgical instrument carrying a plurality of trackable markers.

12. An image guided surgery system comprising,
- a registration artifact including a plurality of imageable fiducials arranged in a known geometric pattern and a plurality of trackable markers disposed in a known geometric relationship to the fiducials;
- a fluorographic camera which is movably mounted to capture a first fluoroscopic image of a patient and the imageable fiducials with the registration artifact in a first location and a second fluorographic image of the patient and the imageable fiducials with the registration artifact in a second location;
- a tracking system which determines positions of the trackable markers with respect to a known coordinate frame, the tracking system being separate from the patient and a fluoroscope; and,
- a computer programmed to:
  - determine positions of the trackable markers with respect to the known coordinate frame when the artifact is in the first location using an output of the tracking system,
  - determine positions of the trackable markers with respect to the known coordinate frame when the artifact is in the second location using the output of the tracking system,
  - determine positions of the imageable markers in the first and second fluorographic images from the determined positions of the trackable markers in the first and second images and the known relationship between the imageable fiducials and the trackable markers, and
- registering the first and second fluorographic images.

* * * * *